(12) United States Patent
Nigam

(10) Patent No.: US 7,657,305 B2
(45) Date of Patent: Feb. 2, 2010

(54) IMPLANTABLE MEDICAL DEVICE FOR IMPROVED STORAGE OF INTRACARDIAC ELECTROGRAMS

(75) Inventor: Indra B. Nigam, Tigard, OR (US)

(73) Assignee: BIOTRONIK CRM Patent AG (CH)

( * ) Notice: Subject to any disclaimer, the term of this patent is extended or adjusted under 35 U.S.C. 154(b) by 452 days.

(21) Appl. No.: 11/563,317

(22) Filed: Nov. 27, 2006

(65) Prior Publication Data

US 2008/0125665 A1    May 29, 2008

(51) Int. Cl.
*A61B 5/04* (2006.01)
*A61B 5/0402* (2006.01)

(52) U.S. Cl. .......................... 600/509; 607/9

(58) Field of Classification Search .......... 600/300, 600/508, 509, 515, 516, 517, 518; 607/9, 607/24; 345/440, 440.1
See application file for complete search history.

(56) References Cited

U.S. PATENT DOCUMENTS 5,836,889 A * 11/1998 Wyborny et al. ............ 600/509
6,599,242 B1 * 7/2003 Splett et al. ................. 600/300

* cited by examiner

*Primary Examiner*—Carl H Layno
*Assistant Examiner*—Pamela M Bays
(74) *Attorney, Agent, or Firm*—Craig A. Fieschko, Esq.; DeWitt Ross & Stevens S.C.

(57) ABSTRACT

An implantable medical device provides for improved storage of recorded IEGMs. A sensing stage is connected to an electrode for picking up electric potentials from inside a heart, the time course of said electric potentials representing a heart signal, a control unit connected to said sensing stage is adapted to process a sequence of data points that each represent an amplitude or magnitude A of a time-varying signal at equidistant points of time t, wherein end points of data segments are determined by processing of the sequence of data points. The control unit is adapted to identify end points of data segments by processing of the sequence of data points.

20 Claims, 12 Drawing Sheets

Example 5-Bit to 4-Bit Encoding Function (for a 16 mV range)

| Original Sample Value(s) | Stored Code Value | Example Real Voltage Represented |
|---|---|---|
| 00000 | 0000 | 0.25 mV (± 0.25 mV) |
| 00001 | 0001 | 0.75 mV (± 0.25 mV) |
| 00010 | 0010 | 1.25 mV (± 0.25 mV) |
| 00011 | 0011 | 1.75 mV (± 0.25 mV) |
| 00100 | 0100 | 2.25 mV (± 0.25 mV) |
| 00101 | 0101 | 2.75 mV (± 0.25 mV) |
| 00110 | 0110 | 3.25 mV (± 0.25 mV) |
| 00111 | 0111 | 3.75 mV (± 0.25 mV) |
| 01000-01001 | 1000 | 4.5 mV (± 0.5 mV) |
| 01010-01011 | 1001 | 5.5 mV (± 0.5 mV) |
| 01100-01101 | 1010 | 6.5 mV (± 0.5 mV) |
| 01110-01111 | 1011 | 7.5 mV (± 0.5 mV) |
| 10000-10011 | 1100 | 9.0 mV (± 1 mV) |
| 10100-10111 | 1101 | 11.0 mV (± 1 mV) |
| 11000-11011 | 1110 | 13.0 mV (± 1 mV) |
| 11100-11111 | 1111 | 15.0 mV (± 1 mV) |

Fig. 7

IMPLANTABLE MEDICAL DEVICE FOR IMPROVED STORAGE OF INTRACARDIAC ELECTROGRAMS

FIELD OF INVENTION

The invention refers to an implantable medical device that stores time-variable signals that are sampled over time. The invention particularly refers to implantable pacemakers and implantable cardioverter/defibrillators featuring automatic capture threshold search and to storing EGM signals in such implant.

BACKGROUND OF THE INVENTION

Implantable medical devices and in particular heart stimulators can be used for treating a variety of heart disorders like bradycardia, tachycardia or fibrillation by way of electric stimulation pulses delivered to the heart tissue, the myocardium. The ability of such devices to pick-up electrical potential in a heart is often times used to acquire an intracardiac electrogram (IEGM) that is a heart signal representing the time course of the electric potential picked up by the implant.

Depending on the disorder to be treated, such heart stimulator generates electrical stimulation pulses that are delivered to the heart tissue (myocardium) of a respective heart chamber according to an adequate timing regime. Delivery of stimulation pulses to the myocardium is usually achieved by means of an electrode lead that is electrically connected to a stimulation pulse generator inside a heart stimulator's housing and that carries a stimulation electrode in the region of its distal end. A stimulation pulse also is called a pace. Similarly, pacing a heart chamber means stimulating a heart chamber by delivery of a stimulation pulse.

In order to be able to sense a contraction a heart chamber that naturally occurs without artificial stimulation and that is called intrinsic, the heart stimulator usually comprises at least one sensing stage that is connected to a sensing electrode on said electrode placed in the heart chamber. An intrinsic excitation of a heart chamber results in characteristic electrical potentials that are picked up via the sensing electrode and that can be evaluated by the sensing stage in order to determine whether an intrinsic excitation—called: intrinsic event—has occurred.

Usually, a heart stimulator features separate stimulation generators for each heart chamber to be stimulated. Therefore, in a dual chamber pacemaker, usually an atrial and a ventricular stimulation pulse generator for generating atrial and ventricular stimulation pulses are provided. Delivery of an atrial or a ventricular stimulation pulse causing an artificial excitation of the atrium or the ventricle, respectively, is called an atrial stimulation event $A_P$ (atrial paced event) or a ventricular stimulation event $V_P$ (ventricular paced event), respectively. The strength of stimulation pulses delivered by the respective stimulation pulse generator is adjustable in order to be able to adjust the stimulation pulse strength to be just sufficient to cause capture (above capture threshold) and thus using as little energy as possible to be effective. Stimulation pulse strength depends on both, duration and amplitude of the stimulation pulse.

Common heart stimulators feature separate sensing stages for each heart chamber to be of interest. In a dual chamber pacemaker usually two separate sensing stages, an atrial sensing stage and a ventricular sensing stage, are provided that are capable to detect intrinsic atrial events $A_S$ (atrial sensed event) or intrinsic ventricular events $V_S$ (ventricular sensed event), respectively.

As known in the art, separate sensing and pacing stages are provided for three-chamber (right atrium RA, right ventricle RV, left ventricle LV) or four-chamber (right atrium RA, left atrium LA, right ventricle RV, left ventricle LV) pacemakers or ICDs.

By means of a sensing stage for a heart chamber to be stimulated, the pacemaker is able to only trigger stimulation pulses when needed that is when no intrinsic excitation of the heart chamber occurs in time. Such mode of pacing a heart chamber is called demand mode. In the demand mode the pacemaker schedules an atrial or a ventricular escape interval that causes triggering of an atrial or ventricular stimulation pulse when the escape interval times out. Otherwise, if an intrinsic atrial or ventricular event is detected prior to time out of the respective atrial or ventricular escape interval, triggering of the atrial or ventricular stimulation pulse is inhibited. Such intrinsic (natural, non-stimulated) excitation are manifested by the occurrence of recognizable electrical signals that accompany the depolarization or excitation of a cardiac muscle tissue (myocardium). The depolarization of the myocardium is usually immediately followed by a cardiac contraction. For the purpose of the present application, depolarization and contraction may be considered as simultaneous events and the terms "depolarization" and "contraction" are used herein as synonyms. The recognizable electrical signals that accompany the depolarization or excitation of a heart chamber are picked up (sensed) by the atrial or the ventricular sensing channel, respectively. Thus, by means of the sensing stages, intracardiac electrogram signals are acquired, that can be evaluated by the implantable medical device. Simple evaluation only checks whether the IEGM exceeds a given threshold in order to detect a sense event. More complex evaluation includes analysis of the IEGM's morphology.

In order to allow for such morphology analysis, it is desirable to record the time course of an IEGM signal by means of sampling the signal. Sampling is carried out by measuring the signals amplitude at predetermined points of time with a constant sampling interval.

In a heart cycle, an excitation of the myocardium leads to depolarization of the myocardium that causes a contraction of the heart chamber. If the myocardium is fully depolarized it is unsusceptible for further excitation and thus refractory. Thereafter, the myocardium repolarizes and thus relaxes and the heart chamber is expanding again. In a typical electrogram (EGM) depolarization of the ventricle corresponds to a signal known as "R-wave". The repolarization of the ventricular myocardium coincides with a signal known as "T-wave". Atrial depolarization is manifested by a signal known as "P-wave". For evaluation of an IEGM it is desirable to be able to determine these particular signals.

With respect to capture control, it is further desirable to have a representation of an IEGM that allows for discrimination between a polarization artifact following an ineffective stimulation pulse and an evoked response following an effective stimulation pulse.

Several modes of operation are available in a state of the art multi mode pacemaker. The pacing modes of a pacemaker, both single and dual or more chamber pacemakers, are classified by type according to a three letter code. In such code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters, and wherein an "O" indicates no sensing occurs. The third letter of the code identifies the action or response that is taken by the pacemaker. In general, three types of action or responses are recognized: (1) an Inhibiting ("I") response wherein a stimulation pulse is delivered to the designated chamber at the conclusion of the appropriate escape interval unless cardiac activity is sensed during the escape interval, in which case the stimulation pulse is inhibited; (2) a Trigger ("T") response wherein a stimulation pulse to a prescribed chamber of the heart a prescribed period of time after a sensed event; or (3) a Dual ("D") response wherein both the Inhibiting mode and Trigger mode may be evoked, e.g., with the "inhibiting" occurring in one chamber of the heart and the "triggering" in the other.

To such three letter code, a fourth letter "R" may be added to designate a rate-responsive pacemaker and/or whether the rate-responsive features of such a rate-responsive pacemaker are enabled ("O" typically being used to designate that rate-responsive operation has been disabled). A rate-responsive pacemaker is one wherein a specified parameter or combination of parameters, such as physical activity, the amount of oxygen in the blood, the temperature of the blood, etc., is sensed with an appropriate sensor and is used as a physiological indicator of what the pacing rate should be. When enabled, such rate-responsive pacemaker thus provides stimulation pulses that best meet the physiological demands of the patient.

A dual chamber pacemaker featuring an atrial and a ventricular sensing stage and an atrial and a ventricular stimulation pulse generator can be operated in a number of stimulation modes like VVI, wherein atrial sense events are ignored and no atrial stimulation pulses are generated, but only ventricular stimulation pulses are delivered in a demand mode, AAI, wherein ventricular sense events are ignored and no ventricular stimulation pulses are generated, but only atrial stimulation pulses are delivered in a demand mode, or DDD, wherein both, atrial and ventricular stimulation pulses are delivered in a demand mode. In such DDD mode of pacing, ventricular stimulation pulses can be generated in synchrony with sensed intrinsic atrial events and thus in synchrony with an intrinsic atrial rate, wherein a ventricular stimulation pulse is scheduled to follow an intrinsic atrial contraction after an appropriate atrioventricular delay (AV-delay; AVD), thereby maintaining the hemodynamic benefit of atrioventricular synchrony.

From the foregoing it becomes apparent that there is a need to provide the physician with a graphical representation of an intracardiac electrogram in order to facilitate heart diagnosis and optimize the mode of pacemaker operation.

The IEGM acquired by the implantable medical device can either be stored in the implant itself or be telemetrically transmitted to a central service center remote from the individual implant. For both cases it is preferred to have as little data as possible to be stored or transmitted. Therefore there is a general need for an effective data representation of a time course of a signal such as an IEGM.

A method for an effective representation of an IEGM is known from U.S. Pat. No. 5,836,889. U.S. Pat. No. 5,836,889 discloses a method and apparatus that identifies turning points in an intracardiac EGM that is sampled at equidistant time points by comparing the slope between an actual sample (n) value and the second last sample (n−1) value with the slope between the actual sample (n) value and the last identified turning point. If the difference between the two slopes thus determined exceeds a predetermined threshold, the second last sample value is marked as a further turning point of the EGM. Once all turning points are thus identified, only the turning points of the EGM signal are stored as a compressed data representation of the EGM signal whereas those sample values not being identified as turning points can be discarded. The slope is determined by determining the difference quotient between two samples. The difference quotient for an actual sample and the second last sample approximately corresponds to the first derivative with respect to time of the EGM signal, because the actual sample and the second last sample are immediate neighbours. The disclosure of U.S. Pat. No. 5,836,889 is included herein by reference.

SUMMARY OF THE INVENTION

It is an object of the invention to provide an implantable medical device that provides for improved storage of recorded IEGMs.

According to the present invention the object of the invention is achieved by an implantable medical device featuring:

a sensing stage connected or being connectable to an electrode for picking up electric potentials inside at least said ventricle of a heart, the time course of said electric potentials representing a heart signal, and a control unit that is connected to said sensing stage.

The control unit is adapted to process a sequence of data points that each represent an amplitude or magnitude A of a time-varying signal at equidistant points of time t, wherein end points of datasegments are determined by processing of the sequence of data points.

The control unit is adapted to identify end points of data segments by a) determination of a first difference quotient $D_1=(A_n-A_{n-1})/(t_n-t_{n-1})$ with respect to an actual data point $A_n$ at $t_n$ and an immediately preceding, second last data point $A_{n-1}$ at $t_{n-1}$, b) determination of second difference quotient $D_2=(A_n-A_e)/(t_n-t_e)$ with respect to an actual data point $A_n$ at $t_n$ and a last end point $A_e$ at $t_e$, said last end point $A_e$ being a previously determined end point or a first data point of said sequence of data points, wherein $t_e$ represents the point of time belonging to said end point, c) selecting the second last data point $A_{n-1}$ as a new end point, if the magnitude (the absolute value) of the difference between the two difference quotients $D_D=D_1-D_2$ exceeds a predetermined first threshold value T, $D_D>T$, and d) determining a data segment length $L=t_n-t_e$ between the point of time $t_n$ of an actual data point $A_n$ and the point of time $t_e$ of a last end point $A_e$, e) and selecting $A_{n-1}$ as a new end point, if said data segment length L exceeds a predetermined maximum length $L_{max}$.

Alternatively, the second difference quotient can be determined based on a second last data point $A_{n-1}$ and $t_{n-1}$ and a last end point $A_e$ at $t_e$:

$$D_2=(A_n-A_e)/(t_n-t_e)$$

Thus, the control unit selects those data points as end points of a data segment, that either meet the selection criteria a), b) and c) or that meet the selection criteria d) and e).

The control unit is further adapted to store every selected end point in association with a segment length between each stored endpoint and an immediately preceding end point as a compressed data representation of said time varying signal.

The difference quotient represents the slope or the first derivative of a straight line crossing the two data points ($A_n$, $t_n$; $A_{n-1}$, $t_{n-1}$ or $A_n$, $t_n$; $A_e$, $t_e$, respectively) for which the difference quotient is determined.

The segment length can be expressed by the number of sampling intervals between the two endpoints of a segment.

The rules for selecting endpoints can alternatively be expressed as follows:

a) a partial quantity of the said obtained signal samples is selected for storage and/or transmission using a set of selection criteria;

b) the said set of selection criteria uses the first derivatives of the signal (or, to be more precise: of a straight line crossing to data points of a time series representing the signal), and for each sample under consideration, two such derivatives are calculated—the current derivative and the segment derivative;

c) wherein the said current derivative is that of the straight-line connection between the (n)th and the (n−1)th signal sample—(n)th sample being the sample under consideration, d) and the said segment derivative is that of the straight-line connection between the (n)th signal sample and the last-stored and/or last-transmitted signal sample;

e) wherein the said set of selection criteria consists of at least the following three rules
  i. the storage condition is met if the magnitude of the difference of the current and the segment derivatives is above a predetermined limit (T),
  ii. the storage condition is met if the said current derivative is zero and the magnitude of the said segment derivative is above a predetermined limit (T1),
  iii. the storage condition is met if the segment duration—between the last-stored and/or last-transmitted signal sample and the (n−1)th sample—reaches the value identified as the maximum number that can be stored or transmitted in the allocated 'length' portion of the storable and/or transmittable data word;

f) having found any one of the said rules being met, the (n−1)th signal sample is stored and/or transmitted and is designated as the new last-stored and/or last-transmitted signal sample, g) and the said segment duration is also stored and/or transmitted in the allocated 'length' portion of the data word.

It is to be noted that threshold values T and T1 may be identical, since ii. is a special case of i.

Preferably, the control unit is further adapted to determine whether said first and said second difference quotient are of opposite sign and select the second last data point $A_{n-1}$ as a new end point, if the difference between the two difference quotients $D_D = D_1 - D_2$ exceeds a predetermined second threshold value T2.

In other words: a further storage condition met if the said current and segment derivatives are of opposite polarities and the magnitude of the difference of the current and the segment derivatives is above another predetermined lower limit T2.

The control unit can be further adapted to determine whether a data segment length $L = t_n - t_e$ between the point of time $t_n$ of an actual data point $A_n$ and the point of time $t_e$ of a last end point $A_e$ exceeds a predetermined threshold length L1 and whether the difference between the two difference quotients $D_D = D_1 - D_2$ exceeds a predetermined third threshold value T3, and to select the second last data point $A_{n-1}$ as a new end point, if said two conditions are met.

Regarding the need to set adequate threshold values, the control unit is preferably adapted to determine the first threshold value T, and, if applicable, the second and the third threshold value as a predetermined fraction of a peak amplitude value of said time-varying signal and to redetermine said threshold values if a moving average of said peak amplitude value of said time-varying signal changes.

Depending on whether or not T and T1 are identical, according to a preferred embodiment of the invention, three or four threshold values are to be determined as pointed out above.

In a two channel device providing two sensing stages, e.g. a ventricular sensing stage and an atrial sensing stage, that generate two data sequences, it is preferred to generate a combined compressed data sequence comprising all selected endpoints of both of the data sequences. Therefore, the control unit preferably is adapted to select endpoints of both data sequences and to store every selected endpoint of any of the data sequences together with a corresponding data point of the other data sequence and the segment length between to consecutive endpoints irrespective the data sequence the endpoints belong to. It can be said that thus every data point of one data sequence that corresponds to an endpoint of the other data sequence becomes an endpoint itself—or at least is treated like an endpoint even if it does not fulfill the selection criteria itself.

In order to achieve a further data compression it is preferred that the control unit is adapted to transform each amplitude value (in other words: each selected data point) into a transformed amplitude value prior to storing a selected end point, wherein the transformation is nonlinear such that endpoint values with lower magnitudes are encoded with greater precision, while endpoint values with higher magnitudes are encoded with lesser precision.

With respect to possible downsampling of a sequence of data points it is preferred that the control unit is adapted to downsample an original data sequence in order to generate a data sequence comprising less data points than the original data sequence by dropping one or more points of the original data sequence wherein a point having the largest magnitude of all these mentioned points is retained and the others are dropped, such that all data points representing peak values of the original data sequence are persevered in the downsampled data sequence.

BRIEF DESCRIPTION OF THE DRAWINGS

The above and other aspects, features and advantages of the present invention will be more apparent from the following more particular description thereof, presented in conjunction with the following drawings wherein:

FIG. 7 is a transformation table for nonlinear transformation of amplitude values according to a preferred embodiment of the invention.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
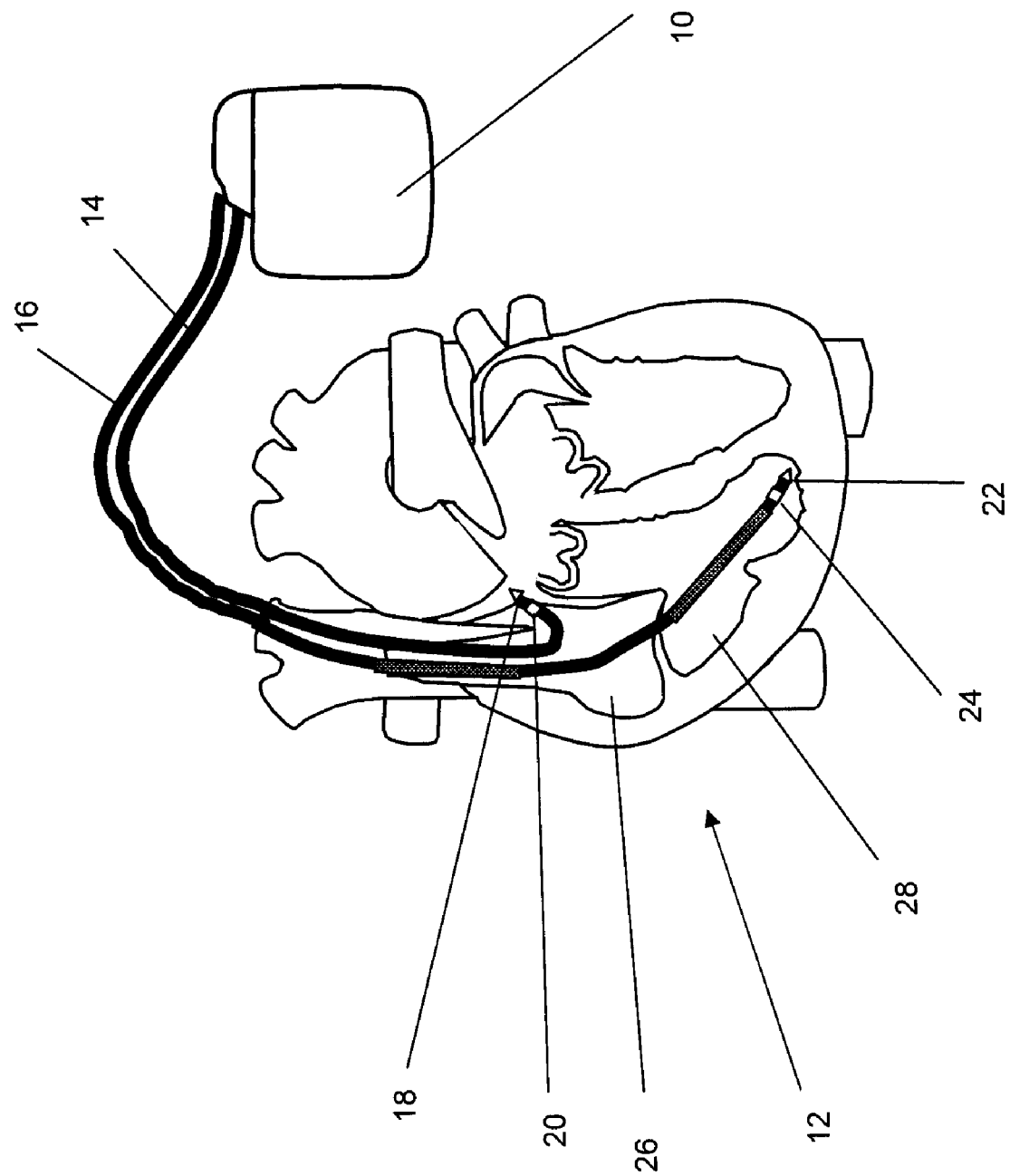
FIG. 1 shows a dual chamber pacemaker connected to leads placed in a heart.

In FIG. 1 a dual chamber pacemaker 10 as heart stimulator connected to pacing/sensing leads placed in a heart 12 is illustrated. The pacemaker 10 is electrically coupled to heart 12 by way of leads 14 and 16. Lead 14 has a pair of right atrial electrodes 18 and 20 that are in contact with the right atria 26 of the heart 12. Lead 16 has a pair of electrodes 22 and 24 that are in contact with the right ventricle 28 of heart 12. Electrodes 18 and 22 are tip-electrodes at the very distal end of leads 14 and 16, respectively. Electrode 18 is a right atrial tip electrode RA-Tip and electrode 22 is a right ventricular tip electrode 22. Electrodes 20 and 24 are ring electrodes in close proximity but electrically isolated from the respective tip electrodes 18 and 22. Electrode 20 forms a right atrial ring electrode RA-Ring and electrode 24 forms a right ventricular ring electrode RV-Ring.

Figure 2:
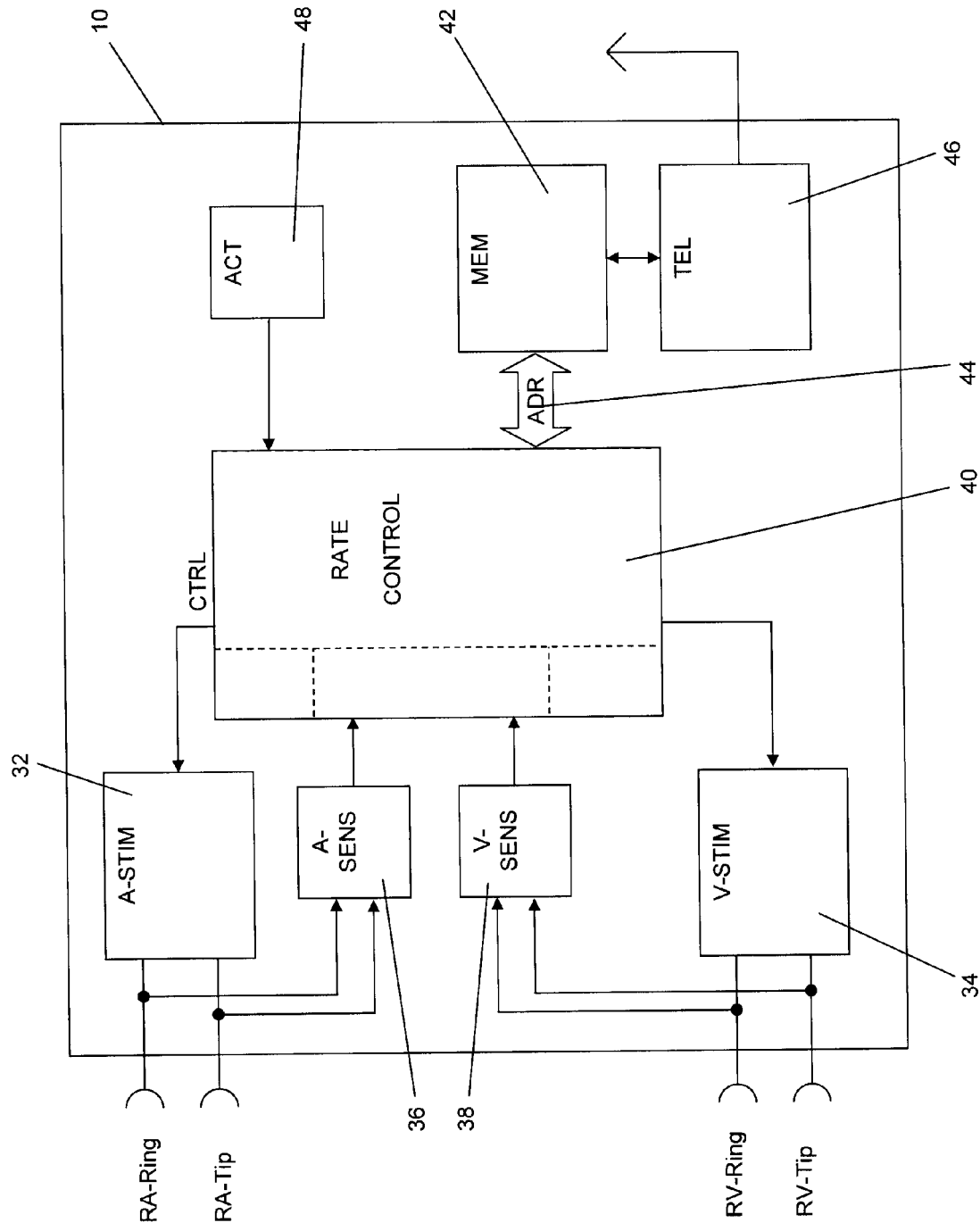
FIG. 2 is a block diagram of a heart stimulator according to the invention.

Referring to FIG. 2 a simplified block diagram of a dual chamber pacemaker 10 is illustrated. During operation of the pacemaker leads 14 and 16 are connected to respective output/input terminals of pacemaker 10 as indicated in FIG. 1 and carry stimulating pulses to the tip electrodes 18 and 22 from an atrial stimulation pulse generator A-STIM 32 and a ventricular pulse generator V-STIM 34, respectively. Further, electrical signals from the atrium are carried from the electrode pair 18 and 20, through the lead 14, to the input terminal of an atrial channel sensing stage A-SENS 36; and electrical signals from the ventricles are carried from the electrode pair 22 and 24, through the lead 16, to the input terminal of a ventricular sensing stage V-SENS 38.

Controlling the dual chamber pacer 10 is a control unit CTRL 40 that is connected to sensing stages A-SENS 36 and V-SENS 38 and to stimulation pulse generators A-STIM 32 and V-STIM 34. Control unit CTRL 40 receives the output signals from the atrial sensing stage A-SENS 32 and from the ventricular sensing stage V-SENS 34. The output signals of sensing stages A-SENS 32 and V-SENS 34 are generated each time that a P-wave representing an intrinsic atrial event or an R-wave representing an intrinsic ventricular event, respectively, is sensed within the heart 12. An As-signal is generated, when the atrial sensing stage A-SENS 32 detects a P-wave and a Vs-signal is generated, when the ventricular sensing stage V-SENS 34 detects an R-wave.

Atrial and ventricular stimulation pulse generators A-STIM 36 and V-STIM 38, respectively, are adapted to generate electrical stimulation pulses having an adjustable strength that depends on a control signal received from the control unit CTRL 40.

Control unit CTRL 40 also generates trigger signals that are sent to the atrial stimulation pulse generator A-STIM 36 and the ventricular stimulation pulse generator V-STIM 38, respectively. These trigger signals are generated each time that a stimulation pulse is to be generated by the respective pulse generator A-STIM 36 or V-STIM 38. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, A-SENS 32 and/or V-SENS 34, is typically disabled by way of a blanking signal presented to these amplifiers from the control unit CTRL 40, respectively. This blanking action prevents the sensing stages A-SENS 32 and V-SENS 34 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events As recorded shortly after delivery of a ventricular stimulation pulses during a preset time interval called post ventricular atrial refractory period (PVARP) are generally recorded as atrial refractory sense event $A_{rs}$ but ignored.

Control unit CTRL 40 comprises circuitry for timing ventricular and/or atrial stimulation pulses according to an adequate stimulation rate that can be adapted to a patient's hemodynamic need as pointed out below.

Still referring to FIG. 2, the pacer 10 may also include a memory circuit MEM 42 that is coupled to the control unit CTRL 40 over a suitable data/address bus ADR 44. This memory circuit MEM 42 allows certain control parameters, used by the control unit CTRL 40 in controlling the operation of the pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM 42 for later retrieval and analysis.

A telemetry circuit TEL 46 is further included in the pacemaker 10. This telemetry circuit TEL 46 is connected to the control unit CTRL 40 by way of a suitable command/data bus. Telemetry circuit TEL 46 allows for wireless data exchange between the pacemaker 10 and some remote programming or analyzing device which can be part of a centralized service center serving multiple pacemakers.

The pacemaker 10 in FIG. 1 is referred to as a dual chamber pacemaker because it interfaces with both the right atrium 26 and the right ventricle 28 of the heart 12. Those portions of the pacemaker 10 that interface with the right atrium, e.g., the lead 14, the P-wave sensing stage A-SENS 32, the atrial stimulation pulse generator A-STIM 36 and corresponding portions of the control unit CTRL 40, are commonly referred to as the atrial channel. Similarly, those portions of the pacemaker 10 that interface with the right ventricle 28, e.g., the lead 16, the R-wave sensing stage V-SENS 34, the ventricular stimulation pulse generator V-STIM 38, and corresponding portions of the control unit CTRL 40, are commonly referred to as the ventricular channel.

In order to allow rate adaptive pacing in a DDDR or a DDIR mode, the pacemaker 10 further includes a physiological sensor ACT 48 that is connected to the control unit CTRL 40 of the pacemaker 10. While this sensor ACT 48 is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

Now the operation of pacemaker 10 shall be illustrated.

Control unit CTRL 40 is adapted to perform a compression algorithm that includes determination and selection of end points of segments in a series of data (data sequence) that represents the course of time of a signal at equidistant points of time, wherein each data point of the data sequence represents the signal amplitude at the respective point of time.

Figure 3:
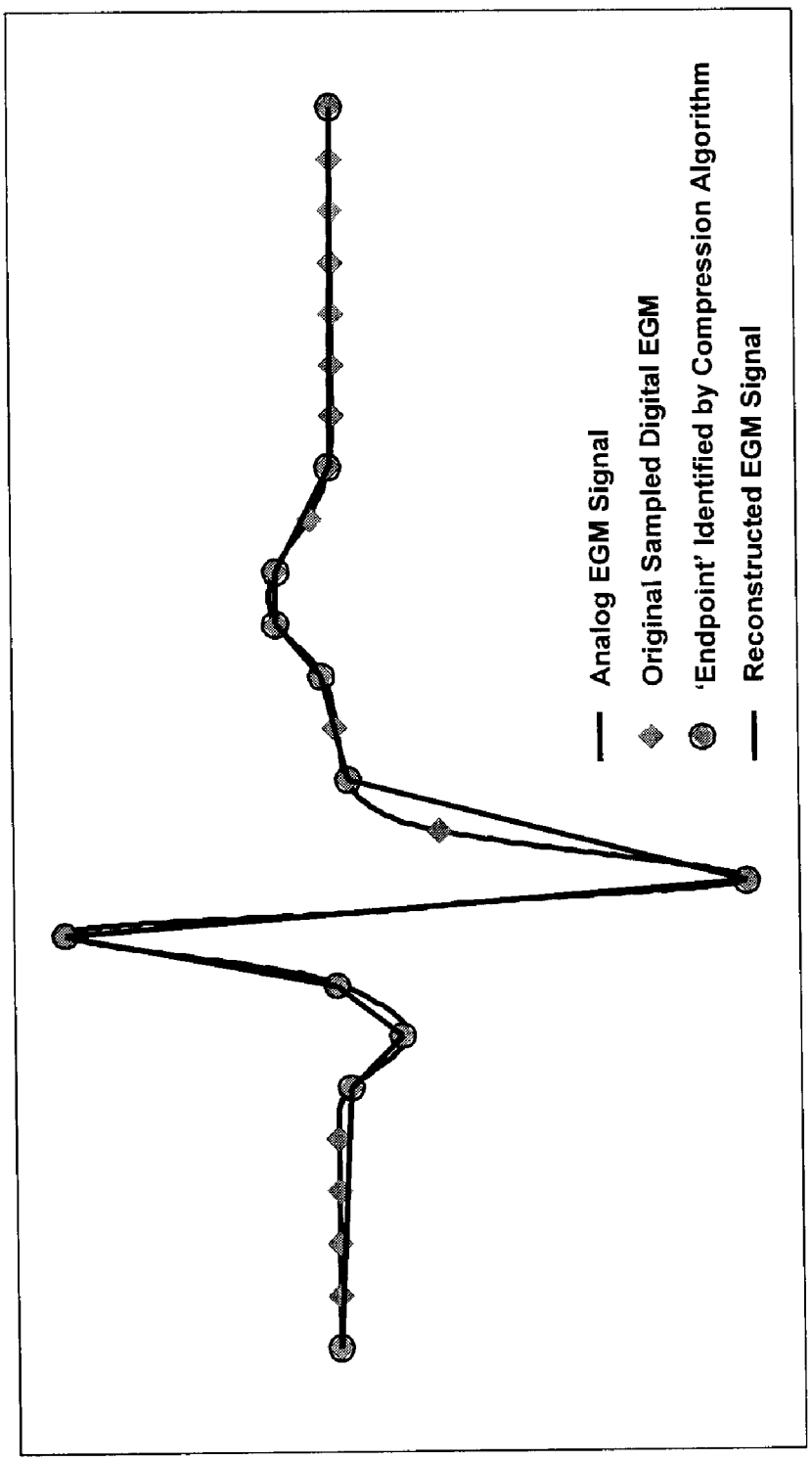
FIG. 3 is a schematic, graphic representation of an EKG signal, along with its representation according to the method of the invention.

The compression algorithm is based on the assertion that if a series of data points can be represented by a single straight line segment for which the location of the line at the points of the intermediate samples cannot deviate from the actual sample values by more than a defined maximum amount, then the intermediate samples can be ignored, and only the values of the endpoints of such segment, and the time between the end points (that is the segment length as represented by the number of sampling intervals forming the segment), need be stored to represent the signal with acceptable accuracy. This is illustrated in FIG. 3.

The identification of the 'Endpoints' is primarily based on identifying changing slope, and secondarily on a maximum segment length.

Figure 4:
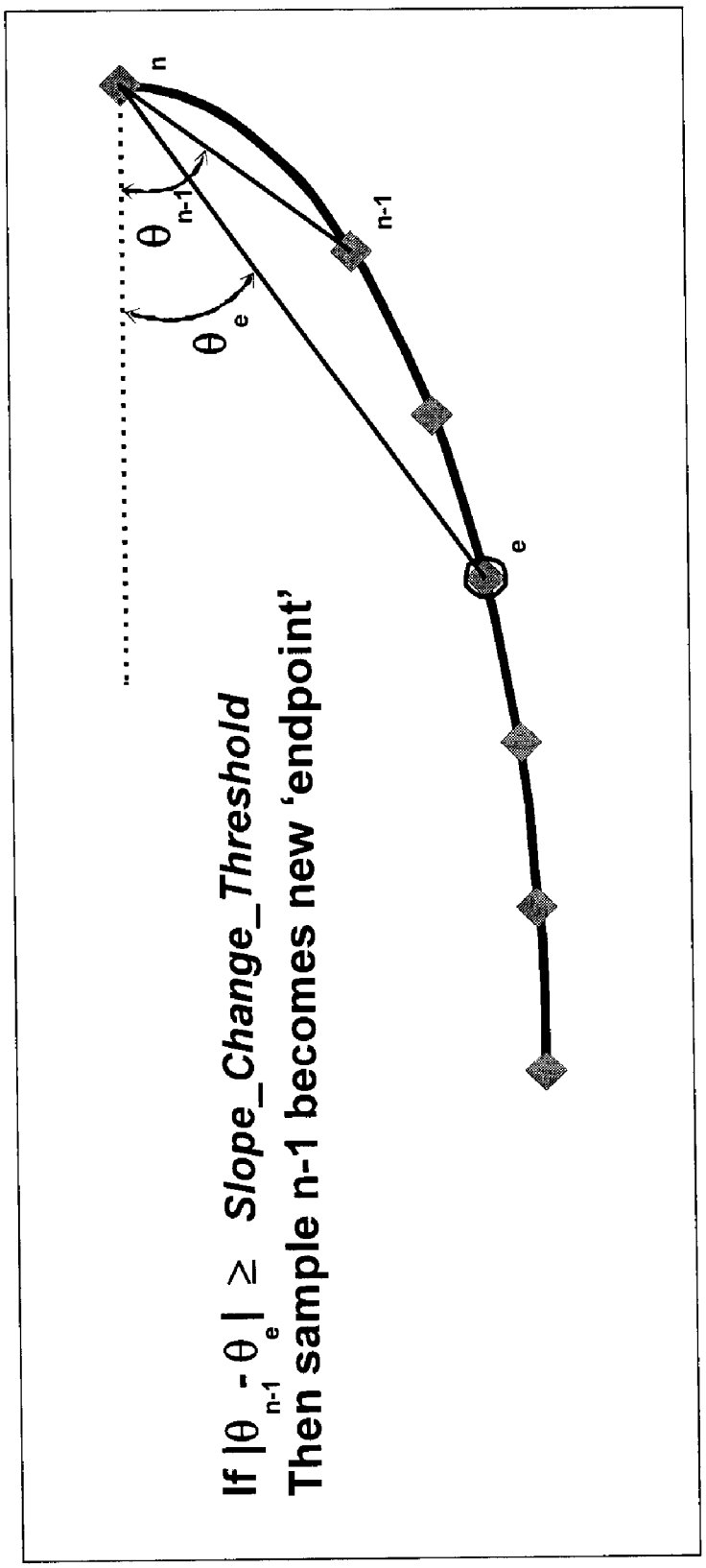
FIG. 4 is graphical representation of a first criterion to select a segment end point according to the invention.

FIG. 4 illustrates how a new 'Endpoint' is identified using one of the criteria described later on. To test for this criterion, the control unit CTRL compares the slope defined by the current (n) and previous (n−1) data samples, to the slope defined by the current data sample (or the previous data sample) and the last identified 'Endpoint' (e). If the magnitude of the difference between these two slopes is equal to or greater than a defined threshold, then the previous data sample is identified as the new 'Endpoint'. Calculation of the slopes is performed by determination of the corresponding difference quotient.

In order to make best use of the physical memory, and to maintain compression efficiency, each 'Endpoint' value that corresponds to the heart signal's magnitude at the particular point of time and its associated segment length are combined in a single data word. Each data word has an endpoint value portion—or, in a dual chamber device, two endpoint value portions—and a segment length portion. This is described for both single channel and dual channel implementations in FIG. 5.

By writing all zeroes in the 'Length' portion in the data word, the 'Endpoint Value' portion of the data word can be used to include useful information such as event identifiers or 'markers' in the compressed data stream. If this data consolidation requires a reduction of the number of endpoint value codes available, a non-linear quantization function is used to represent low valued data points with higher precision, and higher valued data points with lower precision. This quantization function is not specifically described in the FIG. 5, but is discussed in more detail later on with respect to FIGS. 7 and 8.

Figure 6:
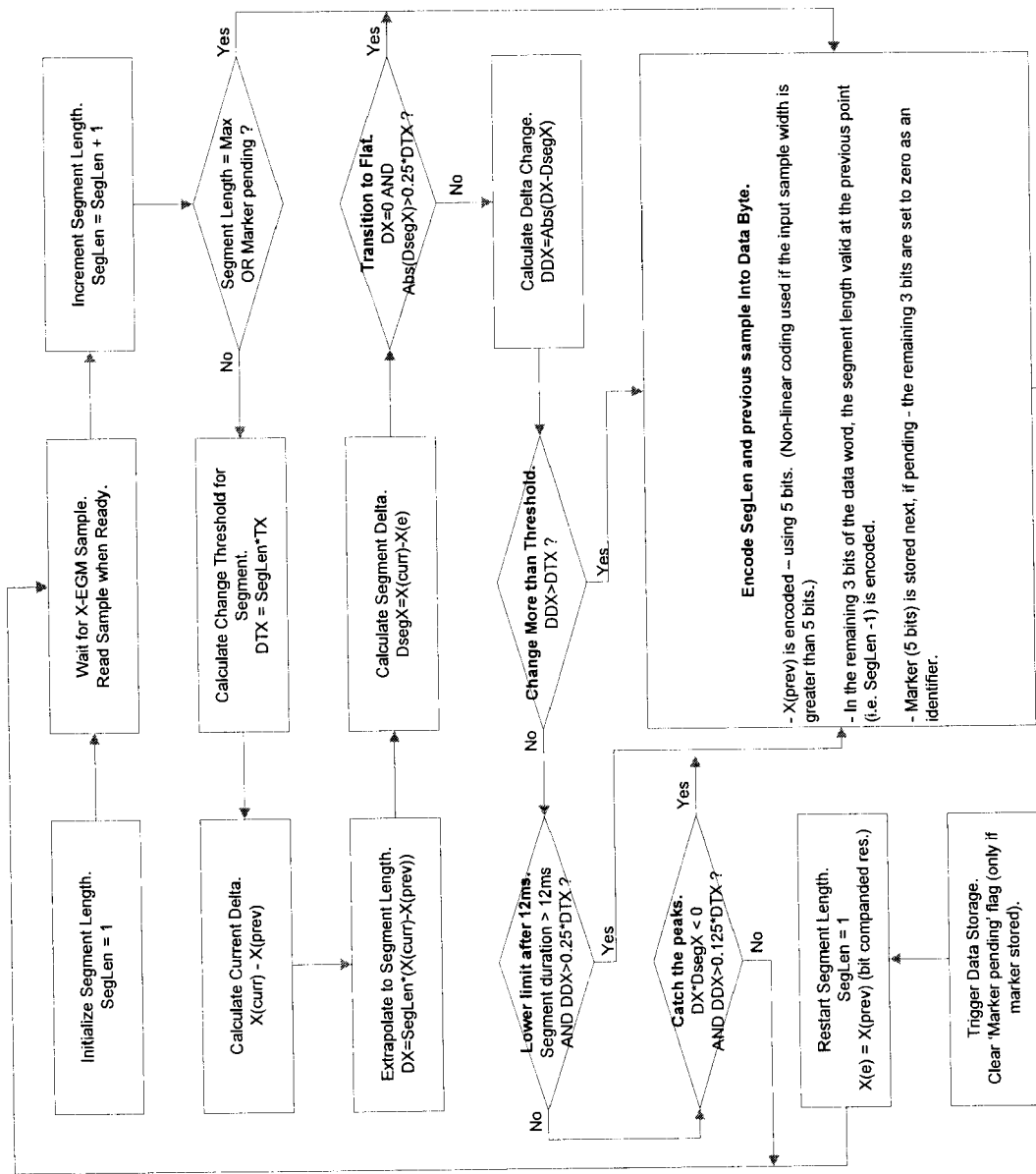
FIG. 6 is a flow chart illustrating selection of 'Endpoints' for a single data sequence.

The compression algorithm is suitable for implementation via embedded software, dedicated hardware, or a combination of the two. In any of these cases, the sequence of operations is the same, and is as described in FIG. 6. The differences lie in the trade-offs between hardware and software resources, and power consumption. In FIG. 6, the letter 'X' has been used to identify the source of the signal, e.g. it can be replaced with an 'A' for atrial signal or with a 'V' for ventricular signal as provided by the atial sensing stage or the ventricular sensing stage, respectively.

Figure 5:
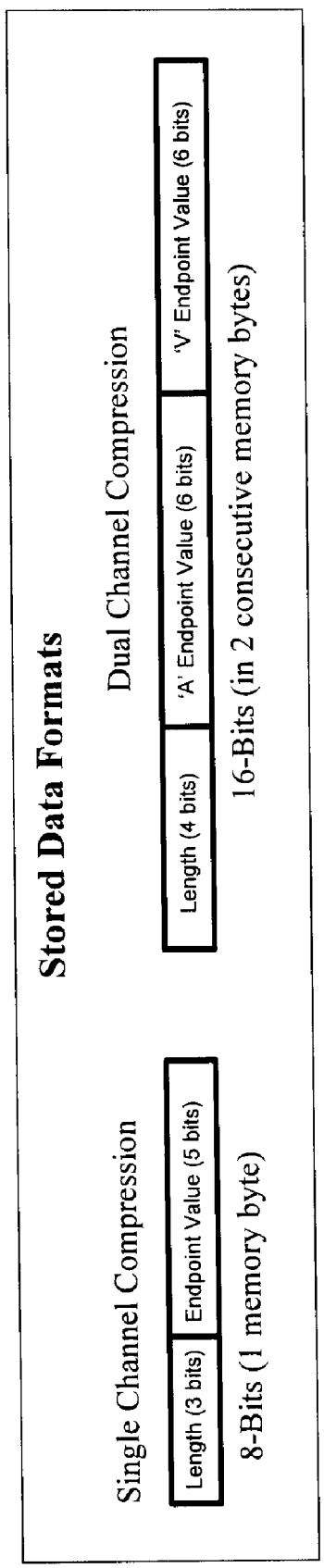
FIG. 5 is a representation of two alternative data formats for storing selected end points according to the invention.
Figure 8:
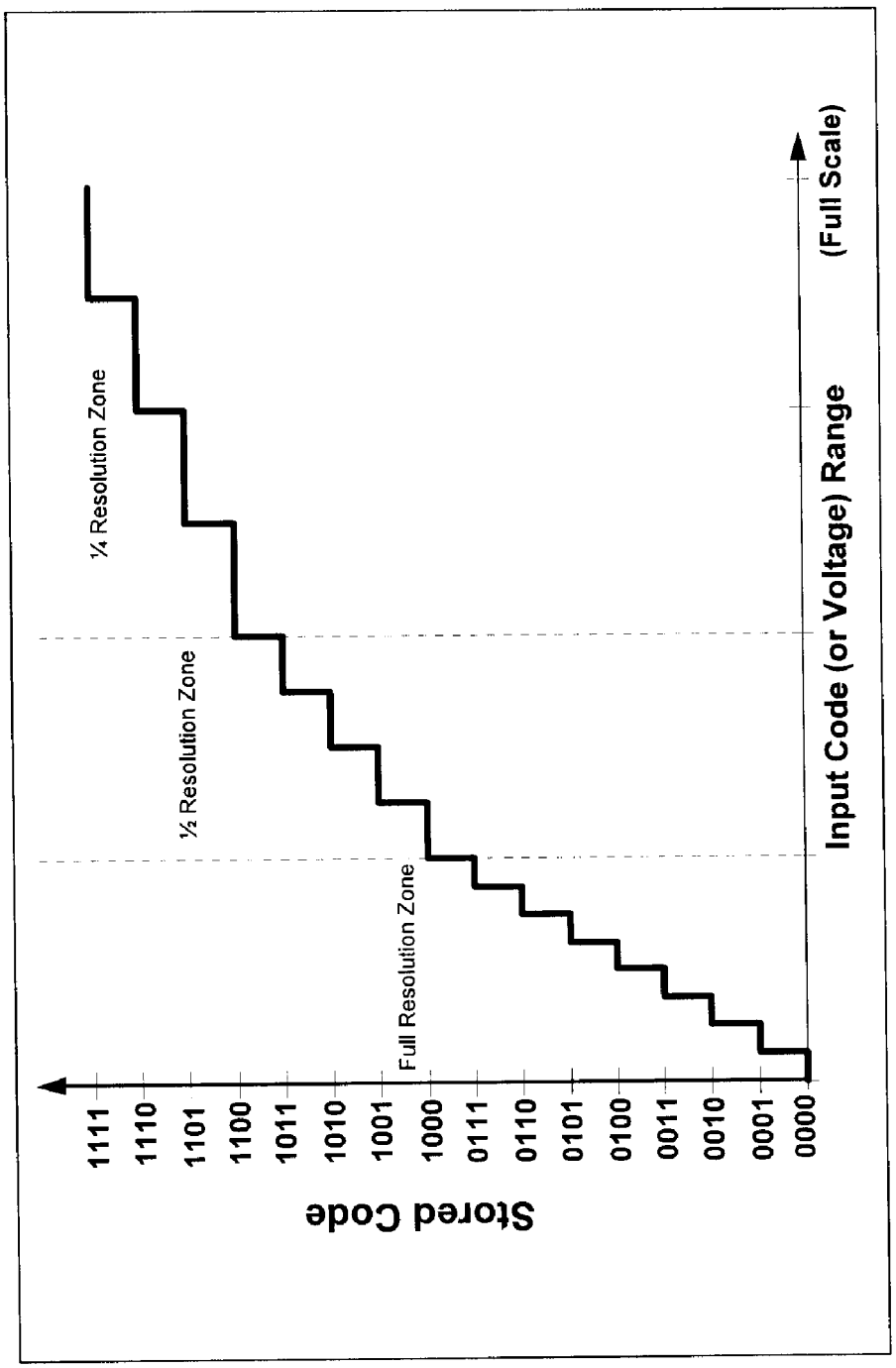
FIG. 8 is a graphical representation of the nonlinear transformation according to FIG. 7.

The non-linear coding, referred to in the text associated with FIG. 5, is a means of dealing with EGM sample bit widths, which might be greater than the available bit-field width in the stored code word. The idea is that endpoint values with lower magnitudes are encoded with greater precision, while endpoint values with higher magnitudes are encoded with lesser precision. The table in FIG. 7 shows an example of this type of function:

This value-to-code mapping function is further illustrated in FIG. 8.

When storing two or more signals simultaneously, as, for example, could be useful in a dual chamber pacemaker, the compression method can be used in either of two ways:

1. Provide separate, independent compression systems to operate on the individual channels. This would result in the greatest overall compression. However, with this approach, the stored data is no longer synchronized, resulting in the requirement of independent memory buffers for the separate channels, as well as more hardware and software tasks for managing the data.
2. Use a single compression system with multiple data pipelines, and enforce synchronization by artificially causing a new 'Endpoint' in all channels whenever an endpoint criterion is met in one of the channels. This conserves hardware and software resources, at the expense of some compression.

Figure 9:
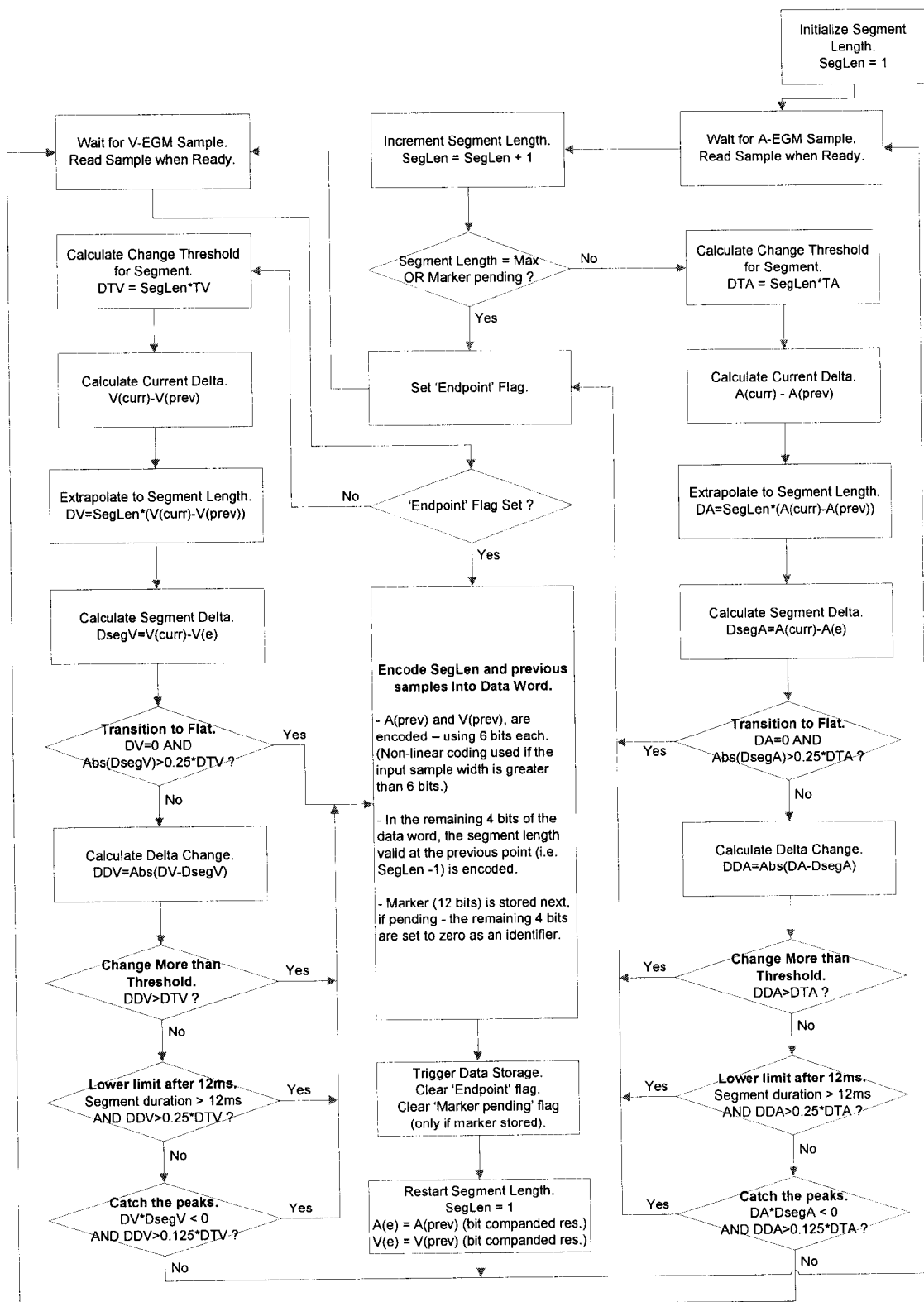
FIG. 9 is a flow chart illustrating selection of 'Endpoints' in a dual channel device such as the dual chamber pacemaker of FIG. 1.

When using the first of these approaches, the flowchart of FIG. 6 applies directly to each channel independently. However, when using the second approach, that flowchart is enhanced, and is shown in FIG. 9 for the case of two channels.

The value used for 'Threshold' (TX, TA and TV in the flowcharts in FIGS. 6 and 9) determines the compression efficiency as well as the quality of the reproduced signal. A smaller value means better quality but lower compression and a larger value means worse quality but higher compression. In the described embodiment, the 'Threshold' value for the individual channel is calculated as a percentage of the peak value of the signal. Furthermore, this value is updated as the signal amplitude varies from one detected heart complex to the next.

When processing the signal data with a goal of storing the compressed signal at a lower sampling rate than the one used for the input signal, the larger of the sample values is retained as against going for a pure decimation where every n:th (n=2 when downsampling to half the sampling rate) sample is retained and all intermediate values simply dropped. This approach helps in retaining the peaks of the signal—of course, together with the other criteria as illustrated in the flowcharts.

Figure 10:
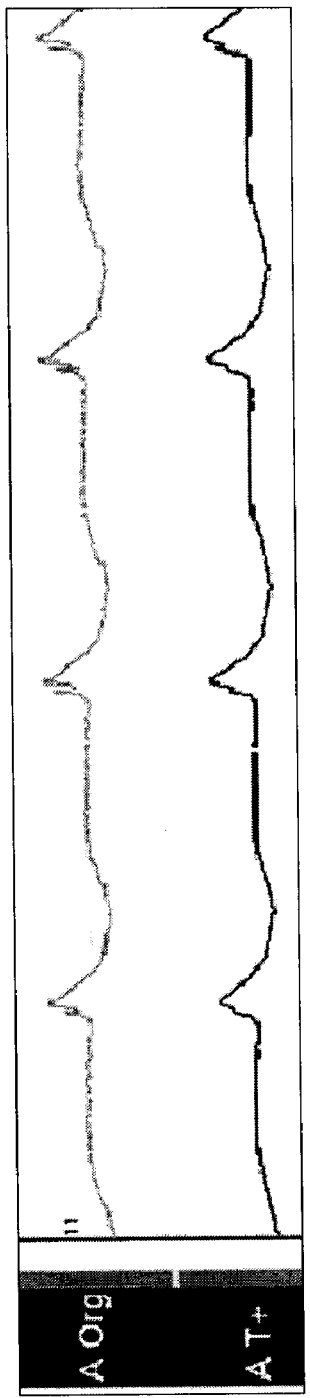
FIG. 10 is an example of an original atrial IEGM together with a representation of the compressed atrial IEGM. The compressed IEGM is marked T+.
Figure 11:
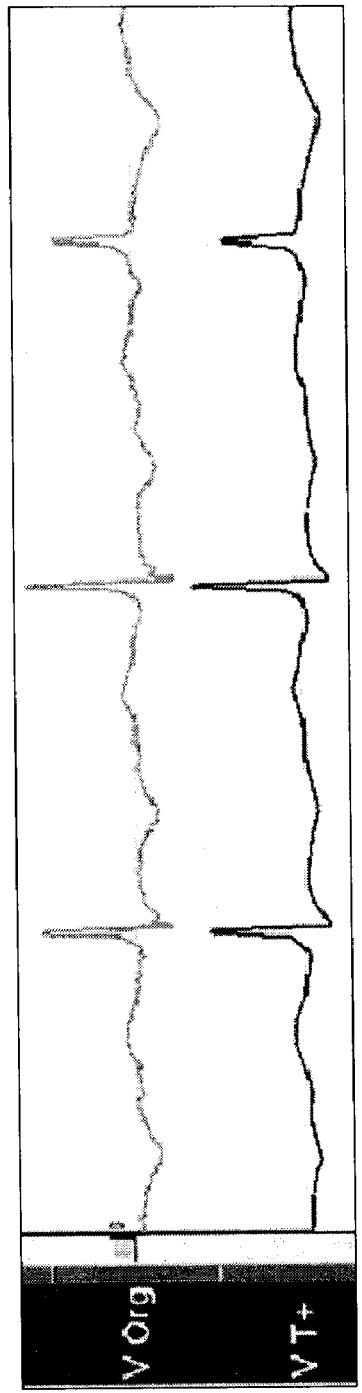
FIG. 11 is an example of an original ventricular IEGM together with a representation of the compressed ventricular IEGM.
Figure 12:
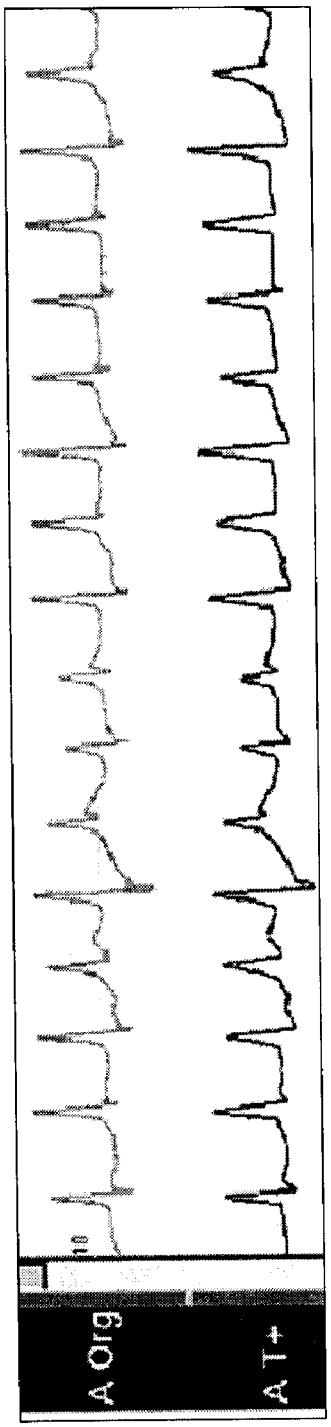
FIG. 12 is another example of an original atrial IEGM together with a representation of the compressed atrial IEGM.
Figure 13:
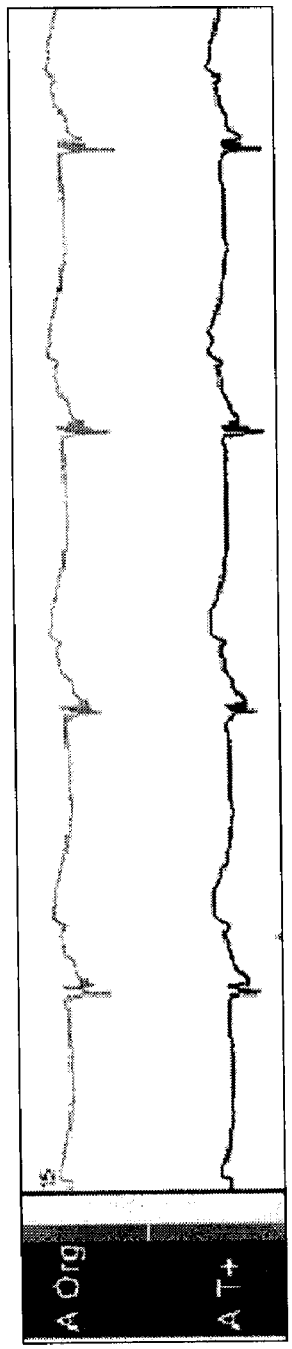
FIG. 13 is a further example of an original atrial IEGM together with a representation of the compressed atrial IEGM.
Figure 14:
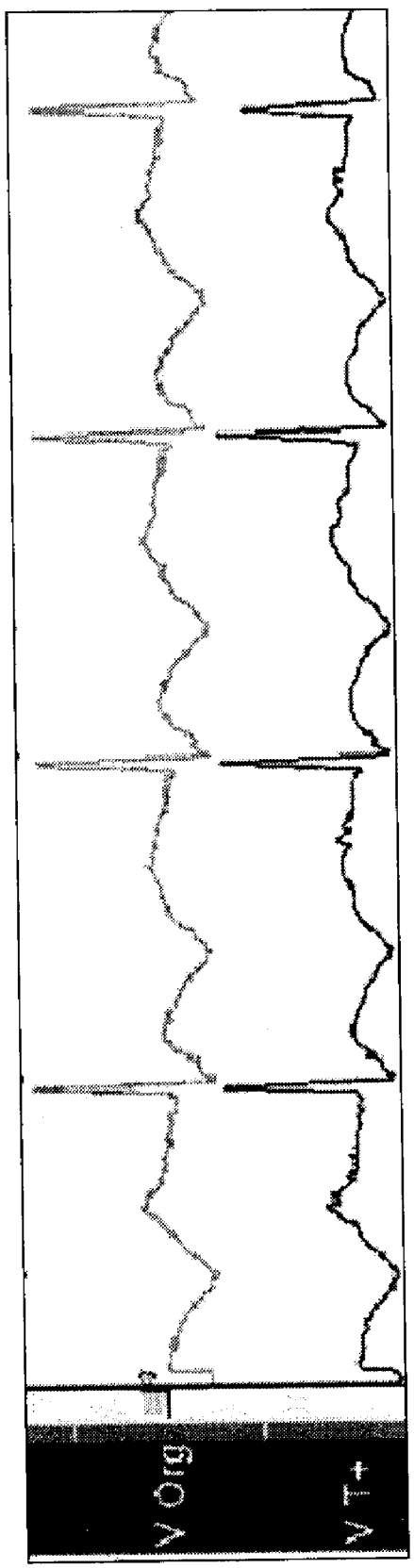
FIG. 14 is a further example of an original ventricular IEGM together with a representation of the compressed ventricular IEGM.

The FIGS. 10 to 14 show some of the resulting compressed signals (labelled as T+) together with the original signal (labelled as 'Org'). The FIGS. 10 to 12 show processing at half of the sampling rate whereas the FIGS. 13 and 14 show processing at full sampling rate. Note that the original signal is always displayed at full sampling rate.

What is claimed is:

1. An implantable medical device comprising:
   at least a sensing stage connected or being connectable to an electrode for picking up electric potentials from inside a heart, the time course of said electric potentials representing a heart signal, said heart signal being sampled in constant sampling intervals and
   a control unit
   that is connected to said sensing stage and
   that is adapted to process a sequence of data points that each represent a magnitude A of a time-varying signal at equidistant points of time t, said processing of the sequence of data points includes:
   determining end points of data segments by
   a) determination of a first difference quotient $D_1=(A_n-A_{n-1})/(t_n-t_{n-1})$ with respect to an actual data point $A_n$ at $t_n$ and an immediately preceding, second last data point $A_{n-1}$ at $t_{n-1}$,
   b) determination of a second difference quotient $D_2$ $(A_n-A_e)/(t_n-t_e)$ or $D_2=(A_{n-1}-A_e)/(t_{n-1}-t_e)$ with respect to an actual data point $A_n$ at $t_n$ or a second last data point $A_{n-1}$ and $t_{n-1}$, respectively, and a last end point $A_e$ at $t_e$, said last end point $A_e$ being a previously determined end point or a first data point of said sequence of data points, wherein $t_e$ represents the point of time belonging to said end point $A_e$,
   c) selecting the second last data point $A_{n-1}$ as a new end point, if the magnitude of the difference between the two difference quotients $D_D=D_1-D_2$ exceeds a predetermined first threshold value T, $D_D>T$, and
   determining a data segment length $L=t_n-t_e$ between the point of time $t_n$ of an actual data point $A_n$ and the point of time $t_e$ of a last end point $A_e$,
   and selecting $A_{n-1}$ as a new end point, if said data segment length L exceeds a predetermined maximum length $L_{max}$,
   and storing said selected end points in association with a segment length between each stored endpoint and an immediately preceding end point as a compressed data representation of said time varying signal.

2. The implantable medical device of claim 1, wherein the control unit is further adapted to:
   determine whether said first and said second difference quotient are of opposite sign and
   select the second last data point $A_{n-1}$ as a new end point, if the magnitude of the difference between the two difference quotients $D_D=D_1-D_2$ exceeds a predetermined second threshold value T2.

3. The implantable medical device of claim 1 or 2, wherein the control unit is further adapted to:
   determine whether a data segment length $L=t_n-t_e$ between the point of time $t_n$ of an actual data point $A_n$ and the point of time $t_e$ of a last end point $A_e$ exceeds a predetermined threshold length L1 and whether the magnitude of the difference between the two difference quotients $D_D=D_1-D_2$ exceeds a predetermined third threshold value T3,
   and to select the second last data point $A_{n-1}$ as a new end point, if said two conditions are met.

4. The implantable medical device of claim 3, wherein the control unit is adapted to determine the first, and, if applicable, the second and the third threshold value as a predetermined fraction of a peak amplitude value of said time-varying signal.

5. The implantable medical device of claim 4, wherein the control unit is adapted to redetermine the first, and, if applicable, the second and the third threshold value if a moving average of said peak amplitude value of said time-varying signal changes.

6. The implantable medical device of claim 1, said implantable medical device having two sensing stages for picking-up and sampling of two heart signals, thus generating two data sequences each representing the time course of a heart signal, wherein the control unit is adapted to select endpoints of both data sequences and to store every selected endpoint of any of the data sequences together with a corresponding data point of the respective other data sequence and the segment length between two consecutive endpoints irrespective the data sequence the endpoints belong to.

7. The implantable medical device of claim 1, wherein the control unit is adapted to transform each magnitude value into a transformed magnitude value prior to storing a selected end point, wherein the transformation is nonlinear such that endpoint values with lower magnitudes are encoded with greater precision, while endpoint values with higher magnitudes are encoded with lesser precision.

8. The implantable medical device of claim 1, wherein the control unit is adapted to downsample an original data sequence in order to generate a data sequence comprising less data points than the original data sequence, wherein a data point of the original data sequence that has the largest magnitude among a number of data points eligible for being dropped is retained and the others are dropped.

9. The implantable medical device of claim 1, wherein the control unit is adapted to determine the first threshold value as a predetermined fraction of a peak amplitude value of said time-varying signal.

10. The implantable medical device of claim 2, wherein the control unit is adapted to determine the first, and, if applicable, the second threshold value as a predetermined fraction of a peak amplitude value of said time-varying signal.

11. A method of deriving, within an implantable medical device, a compressed data representation of a time varying signal from a sequence of data points that each represent an amplitude A of the time-varying signal at equidistant points of time t, said method comprising the steps of:
   determining end points of data segments by
   a) determination of a first difference quotient $D_1=(A_n-A_{n-1})/(t_n-t_{n-1})$ with respect to an actual data point An at tn and an immediately preceding, second last data point $A_{n-1}$ at $t_{n-1}$,
   b) determination of a second difference quotient $D_2=(A_n-A_e)/(t_n-t_e)$ or $D_2=(A_{n-1}-A_e)/(t_{n-1}-t_e)$ with respect to an actual data point An at $t_n$ or a second last data point $A_{n-1}$ and $t_{n-1}$, respectively, and a last end point $A_e$ at $t_e$, said last end point $A_e$ being a previously determined end point or a first data point of said sequence of data points, wherein $t_e$ represents the point of time belonging to said end point $A_e$,
   c) selecting the second last data point $A_{n-1}$ as a new end point, if the difference between the first and the second difference quotients $D_D=D_1-D_2$ exceeds a predetermined threshold value T, $D_D>T$, and
   determining a data segment length $L=t_n-t_e$ between the point of time $t_n$ of an actual data point $A_n$ and the point of time $t_e$ of a last end point $A_e$,
   and selecting $A_{n-1}$ as a new end point, if said data segment length L exceeds a predetermined maximum length Lmax,
   and storing all selected end points in association with a segment length between each stored endpoint and an immediately preceding end point as a compressed data representation of said time varying signal.

12. The method of claim 11, wherein the method further comprises the steps of:
- determining whether said first and said second difference quotient are of opposite sign and
- selecting the second last data point $A_{n-1}$ as a new end point, if the magnitude of the difference between the two difference quotients $D_D = D_1 - D_2$ exceeds a predetermined second threshold value T2.

13. The method according to claim 11 or 12, wherein the method further comprises the steps of:
- determining whether a data segment length $L = t_n - t_e$ between the point of time $t_n$ of an actual data point $A_n$ and the point of time $t_e$ of a last end point $A_e$ exceeds a predetermined threshold length L1 and whether the magnitude of the difference between the two difference quotients $D_D = D_1 - D_2$ exceeds a predetermined third threshold value T3,
- and selecting the second last data point $A_{n-1}$ as a new end point, if said two conditions are met.

14. The method according to claim 13, wherein the method further comprises the step of determining the first, and, if applicable, the second and the third threshold value as a predetermined fraction of a peak amplitude value of said time-varying signal.

15. The method of claim 14, wherein the method further comprises the step of redetermining the first, and, if applicable, the second and the third threshold value if a moving average of said peak amplitude value of said time-varying signal changes.

16. The method according to claim 11, said method being adapted to process two or more data sequences each representing the time course of a heart signal, wherein the method comprises the steps of selecting endpoints in any of the data sequences and storing every selected endpoint of anyone of the data sequences together with corresponding data points of the other data sequences and the segment length between two consecutive endpoints irrespective the data sequence the endpoints belong to.

17. The method of claim 11, wherein the method comprises a step of value-to-code transformation that is carried out prior to storing an endpoint or another data point representing a signal amplitude value, wherein each magnitude value is nonlinearly transformed into a transformed magnitude code such that endpoint values with lower magnitudes are encoded with greater precision, while endpoint values with higher magnitudes are encoded with lesser precision.

18. The method of claim 11, wherein the method comprises the step of downsampling an original data sequence in order to generate a downsampled data sequence comprising less data points than the original data sequence, wherein a data point of the original data sequence that has the largest magnitude among a number of data points eligible for being dropped is retained and the others are dropped.

19. The method according to claim 11, wherein the method further comprises the step of determining the first threshold value as a predetermined fraction of a peak amplitude value of said time-varying signal.

20. The method according to claim 12, wherein the method further comprises the step of determining the first, and, if applicable, the second threshold value as a predetermined fraction of a peak amplitude value of said time-varying signal.

* * * * *